| United States Patent [19] | [11] Patent Number: 4,540,579 |
| Afonso et al. | [45] Date of Patent: * Sep. 10, 1985 |

[54] 2-[(R) AMINO ACID ALKYL]PENEMS

[75] Inventors: Adriano Afonso, West Caldwell; Jay Weinstein, Upper Montclair, both of N.J.

[73] Assignee: Schering Corporation, Kenilworth, N.J.

[ * ] Notice: The portion of the term of this patent subsequent to Sep. 10, 2002 has been disclaimed.

[21] Appl. No.: 441,988

[22] Filed: Nov. 16, 1982

[51] Int. Cl.³ .................. C07D 499/00; A61K 31/425
[52] U.S. Cl. .............................. 514/195; 260/245.2 R
[58] Field of Search ................. 260/245.2 R; 424/270, 424/271

[56] References Cited

U.S. PATENT DOCUMENTS

| 4,260,618 | 4/1981 | Christensen et al. | 424/263 |
| 4,272,437 | 6/1981 | Menard et al. | 260/245.2 R |
| 4,301,074 | 11/1981 | Christensen et al. | 260/245.2 R |
| 4,431,658 | 2/1981 | Afonso | 260/245.2 R |
| 4,448,782 | 5/1984 | Afonso | 424/270 |

FOREIGN PATENT DOCUMENTS 2013674  8/1979  United Kingdom .

Primary Examiner—Nicholas S. Rizzo
Attorney, Agent, or Firm—Anita W. Magatti; Gerald S. Rosen; Stephen I. Miller

[57] ABSTRACT

Disclosed are 6-(1'-hydroxyethyl)-2-[(R)-amino acid alkyl]penem-3-carboxylic acids and salts thereof having an absolute stereochemisty of 5R,6S,8R. The compounds are useful and potent antibacterial agents and can be formulated into a variety of forms suitable for oral, parenteral or topical use.

18 Claims, No Drawings

2-[(R) AMINO ACID ALKYL]PENEMS

BACKGROUND OF THE INVENTION

There is a continuing need for new antibacterials since wide scale usage of any given antibacterial gives rise to resistant strains of pathogens. In addition, the known antibacterials suffer from the disadvantage of being effective only against certain types of microorganisms. Thus, new antibacterial agents are constantly being sought.

Antibacterials of the penem-type are known in the art. See, for instance, U.S. Pat. Nos. 4,301,074 (1981); 4,272,437 (1981) and 4,331,676 (1982).

DESCRIPTION OF THE INVENTION

This invention relates to novel 2-[(R)-amino acid alkyl]penems and to their use as antibacterial agents. More particularly, this invention concerns (5R,6S,8R)-6-(1'-hydroxethyl)-2-(amino acid alkyl)penem-3-carboxylic acids and the salts thereof represented by the formula

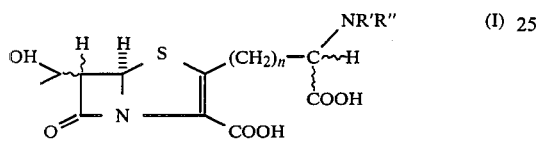

wherein

R' and R" are independently hydrogen, lower alkyl, lower alkenyl, phenyl, substituted phenyl wherein the substituents are one or more groups chosen from among chloro, bromo, fluoro, lower alkyl, hydroxy, nitro, amino, aminomethyl, lower monoalkylamino, lower dialkylamino, lower alkoxy and carboxy, heteroaryl, or R' is hydrogen and R" is acyl, or R',R" and the N to which they are attached form an amidino, substituted amidino, or a guanidino group;

n is 0 to 4; and the pharmaceutically acceptable salts thereof, in racemic in optically active form.

Preferred are compounds represented by the formula

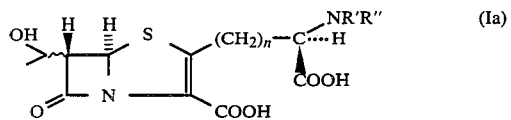

wherein R',R" and n are as defined above.

More preferred are compounds of formula Ia wherein R' and R" are each hydrogen and n is as defined above.

The lower alkyl groups referred to above contain 1–6 carbon atoms and include methyl, ethyl, propyl, butyl, pentyl, hexyl and the corresponding branched chain isomers thereof.

The lower alkenyl groups referred to above contain 2–6, and preferably 2 to 4, carbon atoms, and are, for example, vinyl, allyl, but-2-enyl or but-3-enyl groups.

The term "heteroaryl" as used herein refers to a heterocyclic group of aromatic character which contains 5 to 7 ring atoms of which 3 to 6 are carbon atoms and the remaining ring atoms are nitrogen, sulfur or oxygen atoms. Typical heteroaryl groups are those such as pyridyl, for example, pyrid-2-yl, pyrid-3-yl or pyrid-4-yl, thienyl, for example, thien-2-yl, or furyl, for example, fur-2-yl.

The acyl groups referred to above contain 2–18 carbon atoms and are the residue of a sulfonic acid or a carboxylic acid, such as acetyl, propionyl, valeryl and butyryl.

The amidino and substituted amidino groups referred to above are of the formula

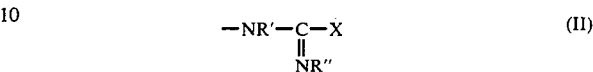

wherein X is hydrogen, lower alkyl or amino and R' and R" are as defined for formula I.

The compounds of the present invention possess four asymmetric carbon atoms, three of which are indicated in formula Ic below as the 5, 6, and 8-position carbon atoms. The compounds may have a (5R,6S,8R) or (5R,6R,8S) configuration at these chiral centers.

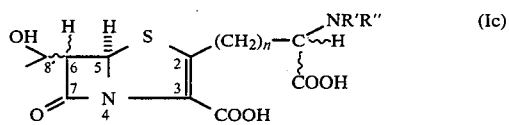

The preferred configuration for these carbon atoms is 5R,6S,8R, and preferably the compound is utilized as its pure optical isomer. Additionally, it has been found that the preferred stereochemistry for the carbon atom in the 2-substituent which bears the amino and the carboxy groups is R when n is 1 to 4 and S when n is 0. However, the use of the diastereomeric form at the amino acid carbon is also envisioned by the present invention. Thus, the present invention is intended to include both the diastereomeric mixture (at the amino acid carbon) and the pure diastereoisomer.

For the purposes of this invention, equivalent to the compounds of formula I are the alkali metal, alkaline-earth metal, amine and acid addition salts. Examples of the alkali metal and alkaline-earth metal salts are the sodium, potassium, aluminum, magnesium and calcium salts. The amine salts may be formed from a wide variety of suitable organic amines, i.e., aliphatic, or aliphatic primary, secondary or tertiary mono-, di- or polyamines, or heterocyclic bases. Specific examples are those salts derived from triethylamine, 2-hydroxyethylamine, di-(2-hydroxyethyl) amine, tri-(2-hydroxyethyl)amine, 4-aminobenzoic acid 2-diethylaminoethyl ester, 1-ethylpiperidine, bicyclohexylamine, N, N'-dibenzylethylenediamine, pyridine, collidine, quinoline, procaine, dibenzylamine, 1-ephenamine and N-alkylpiperidine. Typical acid addition salts are those formed with mineral acids such as hydrochloric, hydrobromic, hydroiodic, phosphoric, sulfuric or with suitable carboxylic acids or sulfonic acids such as trifluoroacetic, p-toluenesulfonic, maleic, acetic, citric, oxalic, succinic, benzoic, tartaric, fumaric, mandelic, ascorbic, lactobionic and malic. Preparation of these salts may be carried out according to conventional procedures for forming salts of beta-lactam antibiotics such as penicillins and cephalosporins.

Preferred compounds of this invention are those wherein n equals 2, i.e., compounds having a 3'-amino-3'-carboxypropyl group as the 2-substituent.

The compounds of this invention are useful in view of their pharmacological properties. In particular, they possess antibacterial activity as evidenced by their ability to inhibit the growth of microorganisms.

The antibacterial activity of the instant compounds may be determined by testing in standardized in vitro dilution tests for minimum inhibitory concentrations (MICs). Using such standard microbiological procedures, the 2-[(R)-amino acid alkyl]penems of this invention are found to exhibit activity against gram-positive and gram-negative bacteria such as *Staphylococcus aureus, Escherichia coli* and *Pseudomonas aeruginosa* at test levels of 0.1 to 100 mcg/ml. Additionally, they show activity against such organisms in the presence of penicillinase and cephalosporinase, indicating a resistance to these enzymes.

As antibacterial agents, the compounds of the present invention are conventionally formulated for oral, parenteral and topical use. Thus, the instant invention includes within it scope pharmaceutical compositions comprising the novel compounds of this invention in admixture with a pharmaceutically acceptable carrier therefor. Additionally, the present invention also provides a method of treating bacterial infections in animals, particularly warm-blooded animals, which comprises administering a compound of formula I or a pharmaceutically acceptable salt thereof, or a pharmaceutical composition there of, to an infected host in an amount sufficient to treat such infection.

The dosage administered of the penems of this invention is dependent upon a variety of factors, i.e., the age and weight of the individual being treated, the mode of administration, and the type and severity of the bacterial infection being prevented or reduced. Typically, the dosage administered 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery systems, e.g. transdermal.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethy cellulose, ethyl cellulose, and methyl cellulose; calcium phosphates such as dicalcium phosphate and tricalcium phosphates; sodium sulfate; calcium sulfate; polyvinyl pyrrolidone. Polyvinyl alcohol; stearic acid; alkaline earth metal stearates such as magnesium stearate; stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols; hydrolyzed cereal solids, water; polyalkylene glycols; isopropanol; gelatin; benzyl alcohol; gums; and petrolatum; as well as other non-toxic compatible fillers, binders, disintegrants and lubricants commonly used in pharmaceutical formulations. Optionally, the compositions may also contain preservatives, aerosol propellants such as hydrocarbons; and coloring, thickening, suspending, dispersing, emlusyfying, wetting, stabilizing and buffering agents. In addition, there may also be included in the composition other active ingredients to provide a broader spectrum of antibacterial activity and/or provide relief of concommittant symptoms such as inflammation.

The compounds of formula I may be prepared by the following reaction Scheme I:

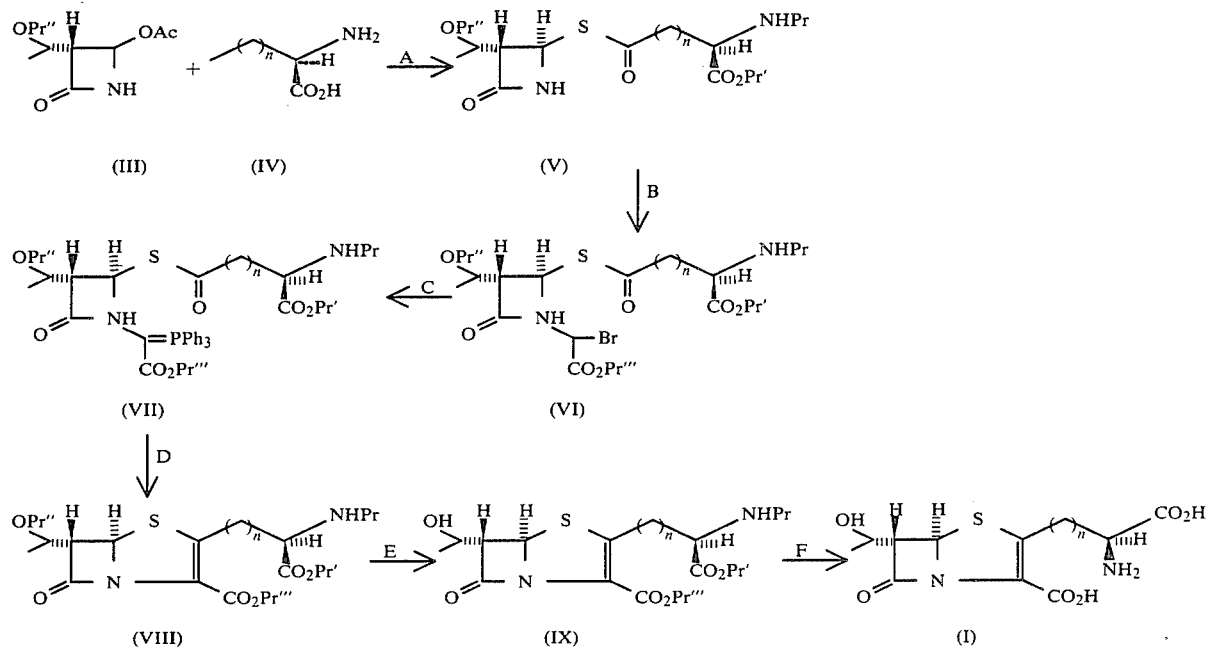

In Step IA, a 4-acetoxy-3-(protected-hydroxyethyl-)azetidin-2-one of formula III wherein Pr″ is a removable hydroxy protecting group is reacted with an alpha-(protected amino)-thiolcarboxylic acid of formula IV wherein Pr and Pr′ are removable protecting groups and n is as hereinbefore defined so as to produce the intermediate of formula V wherein Pr, Pr′,Pr″ and n are as hereinbefore defined. Hydroxy-protecting groups Pr' and Pr" are those known in the art such as t-butoxycarbonyl, 2,2,2,-trichloroethyoxycarbonyl, 2-bromoethoxycarbonyl, or p-nitrobenzyloxycarbonyl, with 2,2,2-tricholorethoxycarbonyl being the general choice of use in the present invention. Typical amino-protecting groups Pr and Pr' are those known in the art such as allyloxycarbonyl 2,2,2,-trichloroethoxycarbonyl, 2-bromoethoxycarbonyl, 4-methoxybenzyloxycarbonyl, t-butoxycarbonyl with the allyloxycarbonyl group being especially preferred for use in the present invention. This reaction is generally conduced in basic aqueous media, typically water to which sodium bicarbonate or sodium hydroxide has been added with the 4-acetoxy-3-protected-hydroxyethylazetidin-2-one of formula III being dissolved first in a water-miscible organic solvent such as tetrahydrofuran or dioxane. Generally, the reaction is conducted at temperatures of 0°–50° C., with room temperature being preferred, and for reaction times of 12–24 hours, depending upon the nature of the reactants and the temperature at which the reaction is conducted.

Step IB of the reaction sequence has 2 parts, the first of which involves the addition of a carboxy-protected 2-hydroxyacetic acid group to the nitrogen of the azetidinone intermediate of formula V. This reaction is accomplished by reacting the intermediate of formula V with a glyoxylic ester of the formula VIa or its hemiacetal of formula VIb

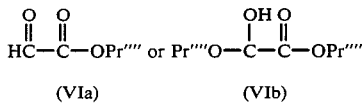

where Pr'''' is a suitable readily removable protecting group. Any readily removable protecting group can be utilized, but preferably one is chosen which can be later removed under the same conditions as Pr, Pr' and/or Pr". For this reason the allyl group is particularly preferred since it can later be removed concurrently with the allyloxycarbonyl group utilized for the amino group of the compound of formula IV. Typically, this reaction is conducted in an organic solvent such as methylene chloride, chloroform or carbon tetrachloride and in the presence of a catalytic amount of an acid acceptor such as triethylamine or pyridine. Typical reaction times vary from about 5–60 minutes, with reaction temperatures being from about 0°–50° C., with room temperatures being generally preferred.

In the second part of Step IB of the reaction sequence, the hydroxy group of the intermediate is replaced by a bromine or chlorine atom to afford the intermediate of formula VI wherein Pr, Pr', Pr", Pr''' and n are as hereinbefore defined. This reaction is accomplished utilizing a halogenating agent such as thionyl chloride or thionyl bromide, a mesyl halide, such as mesyl chloride or bromide, or a phosphorus oxyhalide, especially the chloride, preferably in the presence of a basic (preferably organic) agent such as an aliphatic tertiary amine, for example, triethylamine, pyridine or collidine. Preferably, the reaction is carried out in the presence of a suitable solvent, such as methylene chloride, dioxane or tetrahydrofuran, at temperatures of from about −20° C. to 0° C.

Step IC of the reaction sequence involves the conversion of the halide intermediate of formula VI into the phosphorane intermediate of formula VII wherein Pr, Pr', Pr", Pr''' and n are as hereinbefore defined. This conversion is accomplished by reaction of the intermediate of formula VI with a suitable phosphine compound such as a tri-loweralkylphospine, for example tri-n-butylphosphine, or a triarylphosphine, for example, triphenylphosphine. Triphenylphosphine is generally preferred for use in the present invention. The reaction is preferably carried out in the presence of a suitable inert solvent such as dioxane, tetrahydrofuran or dimethylformamide. Depending upon the reactivity, the reaction is conducted with cooling or at elevated temperatures, preferably at about room temperature.

In Step ID of the reaction sequence, the phosphorane intermediate of formula VII is cyclized to afford the penem intermediate of formula VIII wherein Pr, Pr', Pr", Pr''' and n are as hereinbefore defined. This reaction is accomplished by dissolving the phosphorane intermediate of formula VII in a suitable organic solvent such as benzene, toluene or xylene and heating to reflux temperature for a period of 24–48 hours.

Steps IE and IF involve the removal of the protecting groups Pr, Pr', Pr" and Pr'''. The reaction conditions for deprotection depend on the nature of the protecting groups utilized. For instance, the 2,2,2-trichloroethoxycarbonyl group is preferably removed by treatment with zinc and glacial acetic acid at temperatures of from about −30° to about 0° C. Groups such as p-nitrobenzyloxycarbonyl are removed by hydrogenolysis, for example by treating with hydrogen in the presence of a noble metal catalyst such as palladium. The allyl and allyloxycarbonyl groups, preferred groups for use in the present invention, are most preferably removed utilizing the methods taught in U.S. Pat. No. 4,314,942 to McCombie (1982) which utilize 2-ethylhexanoic acid or an alkali metal salt thereof and a catalytic amount of an organic soluble palladium complex to effect removal of the protecting groups and afford the desired compound of formula I. Additionally, these protecting groups may be removed by the method of Tsuji, taught in Tetrahedron Letters, 7, 613 (1979).

Salts the compounds of formulae I and Ia may be produced by methods well-known in the beta-lactam art. For example, salts of such compounds with acid groups can be formed by treating with metal compounds such as alkali metal salts of suitable carboxylic acids, or with ammonia or a suitable organic amine, wherein preferably stoichiometric amounts or only a small-excess of the salt-forming agent used. Acid addition salts of the compounds of formulae I and Ia with basic groupings are obtained in the usual manner, for example, by treating with an acid or a suitable anion exchange reagent. Inner salts of the compounds of formula, i.e., a zwitterion, may be formed by neutralizing salts such as acid addition salts to the isoelectric point.

Salts may be convented in the usual manner into the free carboxy compounds.

Resulting mixtures of isomers can be separated into the individual isomers according to known methods. Diastereomeric mixtures, for example, can be separated by fractional crystallization, absorption chromatography (column or thin layer) or other suitable separation methods. Resulting racemates can be resolved into the antipodes in the customary manner, for example, by forming a mixture of diastereomeric salts with optically active salt-forming reagents, separating the diastereomeric salts and converting the salts into the free compounds, or by fractional crystallization from optically active solvents.

The starting materials of formula III may be produced by methods known in the art, i.e., according to the methods taught by European Patent Application No. 80810004, published July 23, 1980 or by British Published Application No. 2013674 (1979).

The starting materials of formula IV are produced by first protecting the amino group of an alpha-aminocarboxylic acid of the formula X

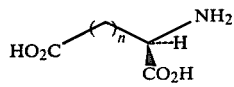 (X)

wherein n is as herebefore defined, to afford the intermediate of the formula XI,

 (XI)

where Pr is a suitable readily removable amino protecting group and n is as hereinbefore defined. Suitable protecting groups are those typically utilized in the beta-lactam art, such as p-nitrobenzyl oxycarbonyl and allyloxycarbonyl. For the purposes of this invention, the allyloxycarbonyl group is a particularly preferred protecting group. Typically, this reaction is conducted in aqueous media to which a suitable inorganic base, such as sodium hydroxide has been added. The protecting group is added via a reactive derivative, such as the chloroformate.

The α-carboxy group of the protected amino compound of formula XI is then protected by a group Pr' as defined above, using methods well known to those skilled in the art (an example of which is described in Procedure C) to give a compound of formula XI(a):

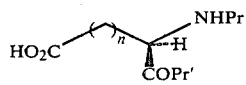 IX(a)

The carboxy group of the compound of formula XI(a) is then converted to a thiolcarboxy group, thus affording the starting material of formula IV. This conversion is typically accomplished by dissolving the compound of formula XI(a) in a suitable solvent, such as tetrahydrofuran or dioxane, and treating it with isobutylchloroformate and an organic acid acceptor such as triethylamine or pyridine, followed by the addition of hydrogen sulfide gas. Typically, the reaction is conducted at temperatures of about −20° to about 0° C. with reaction time of 5-30 minutes being generally sufficient.

Compounds of formula I may also be prepared from racemic starting materials of formula IV (i.e., substitute D,L mixtures for compounds of formula X). The desired isomer may be separated from the mixture using conventional techniques as described above.

An alternate method for the preparation of the compounds of formula I involves the reaction of a compound of formula XI(a) wherein Pr and n are as hereinbefore defined with a silver salt of the formula XII

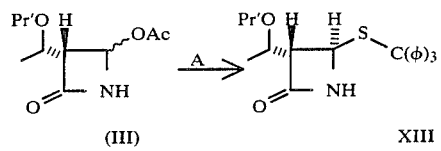 (XII)

wherein Pr'' and Pr''' as hereinbefore defined to afford the intermediate of formula VII which is then subjected to the same steps as hereinabove described to give the compounds of formula I. This reaction is typically conducted in an inert solvent such as tetrahydrofuran or ethyl ether at temperatures of from about −20° to about 0° C. Reaction times vary from about 0.5 to 2 hours.

Preferably the compound of formula XI is prepared in situ in the reaction media by contacting a compound of formula XI with a chloroformate agent, such as isobutyl chloroformate, and an acid acceptor, such as pyridine or triethylamine. The resultant compound of formula XI is then immediately reacted with the silver salt of formula XII.

The silver salt of formula XII is prepared by the following reaction Scheme II:

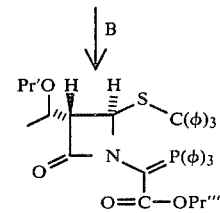

Step II A of this reaction Scheme involves the conversion of the starting material of formula III to a 2-triphenylmethyl thio azetidinone intermediate of the formula XIII wherein Pr' is as hereinbefore defined. This is accomplished by reacting the compound of formula III with triphenylmethylthiol in the presence of an acid acceptor. Either an inorganic, such as potassium or sodium carbonate, or organic, such as triethylamine, acid acceptor can be utilized. Typically, the reaction is conducted at temperatures of 0°-50° C. with room temperatures being preferred. Preferably, an organic solvent such as acetonitrile or pyridine is utilized. Reaction times typically vary from about 2-24 hours, depending upon the other reaction conditions utilized.

In Step II B of this reaction scheme, the intermediate of formula XIII is converted to the phosphorane intermediate of formula XIV. This is accomplished in a manner essentially as described above for the conversion of the intermediate of formula V to the intermediate of formula VII, utilized similar, if not identical, reaction conditions and reagents.

The final step, Step III C, involves the conversions of the intermediate of formula XIV to the silver salt intermediate of formula XII. Typically, this reaction is conducted in a suitable organic solvent such as a halogenated hydrocarbon such as methylene chloride. The silver reagent is generally a salt such as silver nitrate. Any salt which forms a soluble salt in the selected solvent can be utilized. An organic or inorganic base, such as aniline, pyridine, collidine or an alkali metal carbonate is added to the reaction mixture. Preferably, the temperature range is from about −20° to about 25° C. Reaction times vary, depending upon the particular conditions and reagents employed, but are generally less than ½ hour.

The following examples describe in detail compounds and compositions illustrative of the present invention and methods which have been described for their protection. It will be apparent to those skilled in the art that many modifications, both of materials and methods, may be practiced without departing from the purpose and intent of this disclosure.

PREPARATION A

(3S,4R,5R) 4-Acetoxy-3-(1-trichloroethoxycarbonyloxyethyl)azetidin-2-one.

A. To a solution of 100 g 6-β-aminopenicillanic acid in 1200 ml 2.5N sulfuric acid is added 150 g sodium bromide. To the stirred solution at 0° C. is added simultaneously 40 g sodium nitrate in 150 ml water and 40 ml bromine. The addition is completed in 10 minutes, maintaining the temperature at 0° to 5° C. The mixture is then stirred rapidly for 1 hour, then filtered. The filter cake is washed with water and taken up in 600 ml ethyl acetate. The ethyl acetate solution is washed with water, cold dilute sodium bisulfite solution and then again with water. After drying over anhydrous sodium sulphate, the solvent is removed under vacuum to afford 67 g in 85:15 ratio (by NMR data) of 6,6-dibromopenicillanic acid and 6α-bromopenicillanic acid having:

IR: 1728 cm$^{-1}$ and 1800 cm$^{-1}$ (chloroform solution).
NMR: δ=5.7,(1H,s); 4.5, (1H,s); 1.55–1.67, (6H).

B. To a solution of 67 g in 85:15 ratio of 6,6-dibromopenicillanic acid to 6α-bromopenicillanic acid in 500 ml dimethylformamide at 0° C. is added 37.3 g finely powdered potassium carbonate. The solution is stirred 5–10 minutes and 38.3 g methyl iodide is added. The reaction mixture is then stirred for 2 hours allowing the temperature to come to ambient. The reaction is followed by thin layer chromatography eluting with methylene chloride. When complete, the reaction is decanted and the solvent removed under high vacuum to leave 100 ml of solution. To this is added 600 ml ethyl acetate. The solution is then washed with water, dried over anhydrous sodium sulphate and concentrated under vacuum to afford 63 g crude methyl ester. Subsequently, 48 g of pure methyl 6,6-dibromopenicillanate is isolated from this crude product by high pressure liquid chromatography eluting with methylene chloride. This compound exhibits the following characteristics:

NMR: δ=5.7, (1H,s); 4.48, (1H, s); 3.73, (3H, s); =1.42, (3H, s); 1.59, (3H, s).

C. To a solution of 13.7 g methyl 6,6-dibromopenicillanate in 250 ml dry tetrahydrofuran at −78° C. under nitrogen is added 14.7 ml of 3M methyl magnesium bromide in ethyl ether. After stirring for 30 minutes at −78° C., 8 g of freshly distilled acetaldehyde is added and stirring continued for 45 minutes. The reaction mixture is warmed to −20° C. at which time 50 ml 1M potassium phosphate monobasic is added and stirring continued for 5 minutes. The reaction mixture is then poured into 1 liter cold ethyl acetate and washed once with 150 ml brine solution and twice with 150 ml water. The ethyl acetate layer is separated, dried over anhydrous sodium sulfate and evaporated under vacuum. The products, methyl 6α-bromo-6 β-(1-hydroxyethyl)-penicillanate and methyl 6β-bromo-6 α-(1-hydroxyethyl)penicillanate, are detected by thin layer chromatography eluting with 10% ethyl acetate/chloroform.

D. To a solution of 8.0 g methyl 6-bromo-6-(1-hydroxyethyl)penicillanate in 200 ml 95% ethanol is added 800 ml 10% palladium on calcium carbonate. The solution is shaken under 2 atmospheres hydrogen pressure for 5 hours. Disappearance of starting material is followed by thin layer chromatography eluting with 20% ethyl acetate/chloroform. The catalyst is filtered and 100 ml 1M potassium phosphate buffer at pH 7 is added. The precipitate formed is filtered and washed with ethanol. The ethanol is removed under vacuum and 200 ml ethyl acetate added. After washing twice with 50 ml water, and drying over anhydrous sodium sulfate, the ethyl acetate is removed under vacuum to afford a crude mixture of methyl 6-(1-hydroxyethyl)-penicillanate. Column chromatography of 18 g of said mixture eluting with 20% ethyl acetate affords 6.4 g methyl (5R,6S,8R)-6-(1-hydroxyethyl)-penicillanate having the following spectra:

NMR: δ=2.4–2.7, (1H, d); 4.41, (1H, s); 3.74, (3H, s); 3.2–3.33, (1H); 1.25–1.35, (3H, d); 1.44, (3H, s); 1.61, (3H, s).

E. To a solution of 6.2 g methyl (5R,6S,8R)-6-(1-hydroxyethyl)penicillanate in 60 ml dry methylene chloride at 0° C. under nitrogen is added 3.8 ml pyridine then 3.3 ml β,β,β-trichloroethylchloroformate. The reaction is stirred 15 minutes until all starting material is reacted (as determined by thin layer chromatography with 20% ethyl acetate/chloroform). The solution is poured into 250 ml cold methylene chloride and washed twice with cold 10% phosphoric acid solution, once with cold dilute sodium bicarbonate, and then with water. After drying over anhydrous sodium sulfate, the solvent is removed under vacuum to afford 10.0 g methyl (5R,6S,8R)-6-(1-trichloroethoxycarbonyloxyethyl)penicillanate having the following spectra:

NMR: δ=5.13–5.16, (1H, d); 4.78, (2H, s); 4.43, (1H, s); 3.70 (3H, s); 3.38–3.58, (1H); 1.45–1.63, (9H).

F. To a solution of mercuric acetate (73.35 g) in glacial acetic acid (500 ml) at 80° C. is added methyl (5R,6S,8R)-6-(1-trichloroethoxycarbonyloxyethyl)-penicillinate (50 g) in small lots. After 2 hours, the mixture is filtered, diluted with ethyl acetate (2 L), washed successively with water, 10% sodium bicarbonate solution, and brine and is then dried and evaporated. The resulting (3S,4R,5R)-1-[(2-methyl-1-methoxycarbonyl)-prop-1-enyl]-3-(1-trichloroethoxycarbonyloxyethyl)-4-acetoxyazetidin-2-one is dissolved in acetone (860 ml)

and water (70 ml). The solution is stirred and cooled in ice bath while adding potassium permanganate (23 g). After ½ hour, the solution is diluted with ethylacetate (500 ml) filtered through celite, concentrated to 300 ml, diluted with an equal volume of ethylacetate and washed several times with water. The organic layer is dried and evaporated to afford the title compound having the following spectra:

NMR: $\delta$1.42 (d,J=6 cps); 1.55 (d,J=6 cps); 3.4 (dd,J=2,8 cps); 4.76 (s), 5.86 (d, J=1.5 cps); 5.90 (d,J=3.0 cps).

Preparation B (3R,4S,5R)-Silver-3-(1'-trichloroethoxycarbonyloxy-1'-ethyl)-1-(allyl-2"-triphenylphosphoranylidene-2"-acetate)-2-azetidinone-4-thiolate A. A solution of the title compound of Preparation A (50 g) in acetonitrile (750 ml) is stirred overnight with potassium carbonate (39.6 g) and triphenylmercaptan (59.8 g) under argon. The mixture is filtered, and the filtrate is evaporated to dryness. The resulting crude product is chromatographed on silica gel (540 g). Elution with 10% ethylacetate:hexane affords (3S,4R,5R)-3-(1'-trichloroethoxycarbonyloxyethyl)-4-tritylthio-azetidin-2-one.

B. The product from Step A (55.9 g) in methylene chloride (600 ml) is treated with allyl glyoxylate allyl hemiacetal (17 g) and triethylamine (1.0 g). After stirring for 1 hour the solution is cooled in ice bath, followed by addition of mesyl bromide (62.96 g) in one lot and then dropwise addition of a solution of triethylamine (40 g) in methylene chloride (90 ml) while maintaining the reaction temperature below 2° C. After 1 hour, the reaction mixture is filtered through silica gel (300 g) and the eluates with 5% ethylacetate:methylene chloride are collected and evaporated. The resulting bromo intermediate is dissolved in dimethylformamide (300 ml). Triphenylphosphine (30 g) is added and the reaction is stirred for 15 hours at room temperature under argon blanket. The solution is diluted with ethylacetate (500 ml), washed with 10% aqueous sodium bicarbonate, brine, dried over sodium sulfate and evaporated under reduced pressure. The resulting crude product is chromatographed on silica gel (1.5 kg). Elution with 20% ethylacetate: hexane affords (3S,4R,5R)-3-(1'-trichloroethoxycarbonyloxyethyl)-1-(allyl-2"-triphenylphosphoranylidene-2"-acetate)-4-tritylthio-2-azetidinone.

C. To a mixture of 5.73 g (3S,4R,5R)-3-(1'-trichloroethoxycarbonyloxyethyl)-1-(allyl-2"-triphenylphosphoranylidene-2"-acetate)-4-tritylthio-2-azetidine in 57 ml methanol is added sufficient methylene chloride to cause solution. The solution is then cooled to 0° C. and 0.92 ml pyridine is added followed by the dropwise addition over a 10 minute period of a solution of 1.37 g silver nitrate in 8 ml water. After five minutes, the reaction mixture is poured over 100 ml ice water. The methylene chloride layer is then separated and the remaining water layer is extracted twice with 50 ml portions of ethyl acetate. The methylene chloride layer and ethyl acetate layers are combined, washed five times with 100 ml portions of cold water and then evaporated to give the title compound.

PREPARATION C

N-Allyloxycarbonyl-L-glutamic acid α-allyl ester

A. A solution of L-glutamic acid (6.58 g) in tetrahydrofuran (80 ml) and water (80 ml) containing sodium bicarbonate (11.36 g) is cooled to 4° C. and stirred while adding allykoxycarbonyl chloride (4.25 ml) dropwise during 45 minutes. The mixture is then stirred overnight at room temperature and then diluted with ethylacetate (100 ml). The aqueous phase is separated, acidified with mineral acid and extracted with ethylacetate. The extract is washed with brine, dried and evaporated to give N-allyloxycarbonyl-L-glutamic acid, 8.9 g.

B. A solution of N-allyloxycarbonyl-L-glutamic acid from Step A (8.8 g) in DMF (8 ml) and triethylamine (5.28 ml) is treated with allyl bromide (3.3 ml). The mixture is stirred overnight at room temperature and then diluted with water (150 ml) containing 10% sodium bicarbonate (40 ml). The mixture is washed with ether (2×100 ml), the aqueous layer is separated, acidified with mineral acid and extracted with ether. The latter ether extract is washed with brine, dried and evaporated to dryness to afford the title compound, 4.4 g, $[\alpha]_D^{26} = +0.3°$ c27.7, CHCl$_3$.

Preparation D

The reaction sequence described in Preparation C is applied to D-glutamicacid, L- and D- aspartic acid and DL-α-amino adipic acid to obtain:
N-allyloxycarbonyl-D-glutamic acid α-allyl ester
N-allyloxycarbonyl-L-aspartic acid α-allyl ester
N-allyloxycarbonyl-D-aspartic acid α-allyl ester
N-allyloxycarbonyl-DL-α-aminoadipic acid α-allyl ester Preparation E N-allyloxycarbonyl D-glutamic γ-Thiolacid α-allyl ester A solution N-allyloxycarbonyl D-glutamic acid α-allyl ester (2.7 g) and pyridine (0.8 g) in tetrahydrofuran (30 ml) is cooled to −10° C. and stirred while adding isobutylchloroformate (1.37 g) dropwise. The mixture is stirred at −10° for 20 minutes and then hydrogen sulfide gas is bubbled for 20 minutes. The mixture is allowed to warm up to room temperature and is then diluted with water/10% sodium bicarbonate/ether. The aqueous layer is separated, acidified with mineral acid and extracted with ethyl acetate. The latter extract is washed with brine, dried and evaporated to afford the title compound.

Preparation F

The procedure described in Preparation E is used to convert the protected amino acids described in Preparations C and D to the following thiolacids:
N-allyloxycarbonyl-L-glutamic γ-thiolacid α-allyl ester
N-allyloxycarbonyl-L-aspartic β-thiolacid α-allyl ester
N-allyloxycarbonyl-D-aspartic β-thiolacid α-allyl ester
N-allyloxycarbonyl-DL-α-aminoadipic δ-thiolacid α-allyl ester.

Preparation G (4R,3S,5R,4'R)
3-(1-trichloroethoxycarbonyloxyethyl)-4-(N-allyloxycarbonyl 4'-amino-4'-carboallyloxy butyroyl)-thio-1-[2"-(allyl-2"-triphenylphosphoranyl acetate)]-azetidin-2-one

METHOD A

Isobutylchloroformate (0.15 ml) is added dropwise to a solution of N-allyloxycarbonyl-D-glutamic acid α-allyl ester (0.32 g) and pyridine (0.1 ml) in dry tetrahydrofuran (3 ml) at −20° C. After 15 minutes, a solution of the title compound of Preparation B (0.8 g) in tetrahydrofuran (8 ml) is added to the reaction mixture which is then stirred at −20° for 1 hour and warmed to room temperature. The mixture is diluted with ethyl acetate, filtered, washed with 5% sodium bicarbonate, dried and evaporated. The crude reaction product is chromatographed on silica gel (20 g). Elution with 40% ethyl acetate/benzene affords the title compound, 0.27 g, $[\alpha]_D^{26} = +2.7°$ (c=0.8, CHCl$_3$).

METHOD B

To a solution of N-allyloxycarbonyl-D-glutamic thiolacid α-allyl ester (2.8 g) and sodium bicarbonate (0.84 g) in water (15 ml) and tetrahydrofuran (15 ml) is added (3S,4R,5R)-4-acetoxy-3-(1-trichloroethoxycarbonyloxyethyl)azetidin-2-one (3.2 g) and the mixture is then stirred overnight; dilution with water and extraction with ethyl acetate affords (3S,4R,5R)-4-(N-allyloxycarbonyl-D-glutamyl α-allyl ester) thio-3-(1-trichloroethoxycarbonyloxyethyl)-azetidin-2-one. A solution of the latter product in methylene chloride (50 ml) is treated with allylglyoxylate (1.3 g) and triethylamine (0.01 ml). After 30 minutes, the mixture is cooled to −10° C., mesyl bromide (2.4 g) is added in one lot followed dropwise by a solution of triethylamine (1.5 g) in methylene chloride (10 ml) while maintaining the temperature below 5° C. After 30 mins. the reaction mixture is treated with triphenylphosphine (4.0 g) in dimethylformamide (30 ml), the solution is then concentrated to about 30 ml and allowed to stand at room temperature overnight. The reaction is then diluted with water, the crude product is isolated by extraction with ethyl acetate and purified by chromatography on silica gel as described in Method A, to afford the title compound.

Preparation H

Using the appropriate protected amino acid/thiolacid and following the procedures described in Method A or Method B, respectively, of Preparation G, the following compounds are obtained.

(4R,3S,5R,4′S) 3-(1-trichloroethoxycarbonyloxyethyl)-4-(N-allyloxycarbonyl 4′-amino-4′-carboallyloxy butyroyl) thio-1-[2″-(allyl 2″-triphenyphosphoranyl acetate)-azetidin-2-one:
$[\alpha]_D^{26°} = +25.6°$ (c=4.7, CHCl$_3$)

(4R,3S,5R,3′R) 3-(1-trichloroethoxycarbonyloxyethyl)-4-(N-allyloxy carbonyl 3′-amino-3′-carboallyloxy propionyl)thio-1-[2″-(allyl 2″-triphenylphosphoranyl acetate)]-azetidin-2-one:
$[\alpha]_D^{26°} = +9.5°$ (c=0.3, CHCl$_3$)

(4R,3S,5R,3′S) 3-(1-trichloroethoxycarbonyloxyethyl)-4-(N-allyloxycarbonyl 3′-amino-3′-carboallyloxy propionyl)thio-1-[2″-(allyl 2″-triphenyl phosphoranyl acetate)]-azetidin-2-one:
$[\alpha]_D^{26} = +36.8°$ (c=0.3, CHCl$_3$)

(4R,3S,5R,5′RS) 3-(1-trichloroethoxycarbonyloxyethyl)-4-(N-allyloxycarbonyl 5′-amino-5′-carboallyloxy valeryl)thio-1-[2″-(allyl 2″-triphenylphosphoranyl acetate)]-azetidin-2-one.

EXAMPLE 1

A. (5R,6S,8R,3′R) ALLYL 6-(1-TRICHLOROETHOXYCARBONYLOXYETHYL)-2-(N-ALLYLOXYCARBONYL 3′-AMINO-3′-CARBOALLYLOXY)PROPYL-2-PENEM-3-CARBOXYLATE

A solution of the title compound of Preparation G (0.26 g) in toluene (25 ml) is refluxed for 3 hours under nitrogen. The solution is evaporated under reduced pressure and the residue is chromatographed on silica gel (3 g). The title compound (0.141 g) is eluted with ethyl acetate:hexane (2:6).
$[\alpha]_D^{26} = +76.9°$ (c=2.6, CHCl$_3$).
M.S.: m/e 654 (M+).
NMR: δ=1.47 (d, 3H, J=6.6 cps), 1.64-2.42 (m, 2H), 3.87 (dd, 1H, J=2.4, 9 cps), 5.57 (d, 1H, J=2.4 cps).

B. (5R,6S,8R,3′R) ALLYL 6-(1-HYDROXYETHYL)-2-(N-ALLYLOXYCARBONYL 3′-AMINO-3′-CARBOALLYLOXY)PROPYL-2-PENEM-3-CARBOXYLATE

A solution of the title compound of step A of this example (0.187 g) in tetrahydrofuran:water:acetic acid (2:0.5:0.5 ml) is stirred with zinc dust (0.2 g) until thin layer chromatography showed complete reaction. The mixture is diluted with ethyl acetate (30 ml), filtered and the filtrate is washed with brine, aqueous sodium bicarbonate and brine, dried over sodium sulfate and evaporated under reduced pressure. The residue is chromatographed on silica gel (5 g). Elution with 5% acetone-chloroform affords the title compound, 0.14 g, m.p. 67°-68°;
$[\alpha]_D^{26} = +72.3°$ (c=3.25, CHCl$_3$);
IR: 5.62μ;
M.S.: m/e 480 (M+);
NMR: δ=1.21 (d, 3H, J=6 cps), 3.61 (dd, 1H, J=6, 2 cps), 5.47 (d, 1H, J=2 cps).

C. (5R,6S,8R,3′R) 6-(1-HYDROXYETHYL)-2-(3′-AMINO-3′-CARBOXY)PROPYL-2-PENEM-3-CARBOXYLIC ACID, MONOSODIUM SALT

To a solution of the title compound of Step B of this example (80 mg) in 1M pyridinium formate in methylene chloride (2.4 ml) and 1M pyridine in methylene chloride (0.24 ml), is added triphenyl phosphine (0.04 g) and tetrakis palladium triphenylphosphine (0.06 g) under nitrogen. The mixture is stirred for one hour and centrifuged. The solid is washed several times by resuspending and centrifuging, with methylene chloride, ethyl acetate. The solid is then suspended in 0.5M sodium 2-ethyl hexanoate in ethyl acetate for 10 mins. and centrifuged and washed by centrifugation with ethyl acetate and ether to afford the title compound, 34 mg.
$[\alpha]_D^{26} = +105.8°$ (c=4.3, water);
IR: 5.65μ;
NMR: δ=1.27 (d, 3H, J=6 cps), 3.83 (dd, 1H, J=8, 2 cps), 5.61 (d, 1H, J=2 cps).

EXAMPLE 2

(5R,6S,8R,3'S) 6-(1-HYDROXYETHYL)-2-(3'-AMINO-3'-CARBOXY)PROPYL-2-PENEM-3-CARBOXYLIC ACID, MONOSODIUM SALT

A. (4R,3S,5R,4'S) 3-(1-Trichloroethoxycarbonyloxyethyl)-4-(N-allyloxy carbonyl 4'-amino-4'-carboallyloxy butyroyl)thio-1-[2''-(allyl 2''-triphenylphosphoranyl acetate)]-azetidin-2-one of Preparation H is cyclized to the corresponding penem using the procedure described in Step A of Example 1.

$[\alpha]_D^{26} = +100.6°$ (c=3.4, CHCl$_3$);
IR: 5.60μ;
MS: m/e 654 (M+);
NMR: δ=1.52 (d, 3H, J=6 cps), 3.90 (dd, 1H, J=8, 2 cps), 5.60 (d, 1H, 2 cps).

B. The trichloroethoxycarbonyl protective group of the penem of Step A of this example is removed using the procedure described in Step B of Example 1 to afford the corresponding hydroxyethylpenem.

$[\alpha]_D^{26} = +127.5°$ (c=3.6, CHCl$_3$);
IR: 5.62, 5.69–6.02μ;
MS: m/e 480 (M+);
NMR: δ=1.34 (d, 3H, J=6.8 cps), 3.65 (dd, 1H, J=7, 2 cps), 5.54 (d, 1H, 2 cps).

C. The allyl protective groups of the product from Step B are removed using the procedure described in Step C of Example 1 to afford the title compound.

$[\alpha]_D = 110.9°$ (c=2.3, water);
IR: 5.50μ;
NMR: δ=1.25 (d, 3H, J=6 cps), 3.79 (dd, 1H, J=6, 2 cps), 5.53 (d, 1H, J=2 cps).

EXAMPLE 3

(5R,6S,8R,2'R) 6-(1-HYDROXYETHYL)-2-(2'AMINO-2'-CARBOXY)ETHYL-2-PENEM-3-CARBOXYLIC ACID, MONOSODIUM SALT

A. (4R,3S,5R,3'R) 3-(1-Trichloroethoxycarbonyloxyethyl)-4-(allyloxy carbonyl-3'-amino-3'-carboallyloxy propionyl)thio-1-[2''-(Allyl 2''-triphenylphosphoranyl acetate)]-azetidin-2-one of Preparation H is cyclized to the corresponding penem using the procedure described in Step A of Example 1.

$[\alpha]_D^{26} = +81.°$ (CHCl$_3$);
MS: m/e 640 (M+);
NMR: δ=1.50 (d, 3H, J=6 cps), 3.90 (dd, 1H, J=8, 2 cps), 4.80 (S, 2H), 5.61 (d, 1H, J=2 cps).

B. The trichloroethoxycarbonyl protective group of the penem of Step A of this example is removed using the procedure described in Step B of Example 1 to afford the corresponding hydroxyethylpenem.

$[\alpha]_D^{26} = +81.9°$ (c=0.28, CHCl$_3$);
M.S: m/e 466 (M+);
NMR: δ=1.33 (d,3H, J=6 cps), 3.70 (dd, 1H, J=8 cps), 5.58 (d, 1H, J=2 cps).

C. The allyl protective groups of the produce from Step B are removed using the procedure described in Step C of Example 1 to afford the title compound.

$[\alpha]_D^{26} = +124°$ (c=0.36, water);
IR: 5.68μ;
NMR: δ=1.23 (d, 3H, J=6.8 cps), 3.83 (dd, 1H, J=8, 2 cps) 5.58 (d, 1H, J=2 cps).

EXAMPLE 4

(5R,6S,8R,2'S) 6-(1-HYDROXYETHYL)-2-(2'-AMINO-2'-CARBOXY) ETHYL-2-PENEM-3-CARBOXYLIC ACID, MONOSODIUM SALT

A. (4R,3S,5R,3'S) 3-(1-Trichloroethoxycarbonyloxyethyl)-4-(n-allyloxycarbonyl 3'amino-3'-carboallyloxy propionyl)thio-1-[2''-(allyl 2''-triphenylphosphoranyl acetate)]-azetidin-2-one of Preparation H is cyclized to the corresponding penem using the procedure described in Step A of Example 1, $[\alpha]_D^{26} = +98.6°$ (c=0.07, CHCl$_3$);
MS: m/e 640 (M+);
NMR: δ=1.50 (d, 3H, J=6.6 cps), 3.90 (dd, 1H, J=7,2 cps), 5.57 (d, 1H, J=2 cps).

B. The trichloroethoxycarbonyl protective group of the penem of Step A of this example is removed using the procedure described in Step B of Example 1 to afford the corresponding hydroxyethyl penem.

$[\alpha]_D^{26} = +101.6°$ (c=0.3 CHCl$_3$);
MS: m/e 466 (M+);
NMR: δ=1.36 (d, 3H, J=6.6 cps), 3.69 (dd, 1H, J=8, 2 cps), 5.57 (d, 1H, J=2 cps).

C. The allyl protective groups of the product from Step B are removed using the procedure described in Step C of Example 1 to afford the title compound.

$[\alpha]_D^{26} = +49.3°$ (c=o.3, water).
NMR: δ=1.26 (d, 3H, J=7 cps), 3.88 (dd, 1H, J=6, 2 cps), 5.61 (d, 1H, J=2 cps).

EXAMPLE 5

(5R,6S,8R,4'RS) 6-(1-HYDROXYETHYL)-2-(4'-AMINO-4'CARBOXY) BUTYL-2-PENEM-3-CARBOXYLIC ACID, MONOSODIUM SALT

A (4R,3S,5R,5'RS) 3-(Trichloroethoxycarbonyloxyethyl)-4-(n-allyloxycarbonyl 5'-amino-5'-carboallyloxy valeryl)thio-1-[2''-(allyl 2''-triphenylphosphoranyl acetate)]-azetidin-2-one of Preparation H is cyclized to the corresponding penem using the procedure described in Step A of Example 1.

B. The trichloroethoxycarbonyl protective group of the penem of Step A of this example is removed using the procedure described in Step B of Example 1 to afford the corresponding hydroxyethyl penem.

C. The allyl protective groups of the product from Step B are removed by using the procedure described in Step C of Example 1 to afford this title compound.

EXAMPLE 6

(5R,6S,8R,3'R) 6-(1-HYDROXYETHYL)-2-(N-ACETIMIDOYL 3'-AMINO-3'-CARBOXY)PROPYL-2-PENEM-3-CARBOXYLIC ACID, SODIUM SALT

A solution of (5R,6S,8R,3'R) 6-(1-hydroxyethyl)-2-(3'-amino-3'-carboxy)propyl-2-penem-3-carboxylic acid sodium salt from Example 1 (0.3 g) in water (3 ml) is stirred at 10° C. with sodium bicarbonate (0.09 g) and ethylacetimidate (0.1 g) for 30 minutes. The solution is then lyophylized and the crude product is purified by HPLC on C$_{18}$ - silica gel to afford the title compound.
IR: 5.68μ.

EXAMPLE 7

(5R,6S,8R,3'R) 6-(1-HYDROXYETHYL)-2-(3'-GUANIDO-3'-CARBOXY)PROPYL-2-PENEM-3-CARBOXYLIC ACID, SODIUM SALT

A solution of (5R,6S,8R,3'R) 6-(1-hydroxyethyl)-2-(3'amino-3'-carboxy)propyl-2-penem-3-carboxylic acid, sodium salt from Example 1 (0.15 g) in water (1.5 ml) at 10° C. is stirred with sodium bicarbonate (0.040 g) and S-benzyl thiourea hydrochloride (0.083 g) for 1 hour. The solution is then lyophylized and the title compound is obtained by chromatographing the crude lyophylized product on $C_{18}$ - silica gel.

IR: 5.68μ.

In the following Examples 8 to 12, the active ingredient may be (5R,6S,8R,3'R)-6-(1-hydroxyethyl)-2-(3'-amino-3'-carboxy)propyl-2-penem-3-carboxylic acid or an equivalent amount of any of the other compounds of this invention.

EXAMPLE 8

Capsules

| No. | Ingredient | mg/capsule | mg/capsule |
|---|---|---|---|
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
| | Total | 500 | 650 |

Method of Manufacture

Mix Items Nos. 1, 2, 3 and 4 in a suitable mixer for 10-15 minutes. Add Item No. 5 and mix for 1-3 minutes. Fill the mixture into suitable two-piece hard gelatin capsules using encapsulating machine.

EXAMPLE 9

Tablets

| No. | Ingredient | mg/tablet | mg/tablet |
|---|---|---|---|
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
| | Total | 350 | 700 |

Method of Manufacture

Mix Item Nos. 1 and 2 in a suitable mixer for 10-15 minutes. Granulate the mixture with Item No. 3. Past the wet granulation through a coarse screen (e.g., ¼") if needed, and dry the wet granules. Mill the dried granules. Combine Item No. 4 and the dried granules and mix for 10-15 minutes. Add Item No. 5 and mix for 1-3 minutes. Compress the mixture to appropriate size and weight on a suitable tablet machine.

EXAMPLE 10

Injectable Powder: (per vial)

| | g/vial | g/vial |
|---|---|---|
| Active Ingredient | 0.5 | 1.0 |

Add sterile water for injection or bacteriostatic water for injection for reconstitution.

EXAMPLE 11

Injectable Solution

| Ingredient | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion ( 85% of the final volume) of the water for injection at 65°-70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 membrane and fill into appropriate containers.
6. Terminally sterilize the units by autoclaving.

EXAMPLE 12

Injectable Powder: (per vial)

| | g/vial |
|---|---|
| Active Ingredient | 1.0 |
| Sodium Citrate | 0.05 | pH is adjusted to 6.2 using 0.1N citric acid solution.

Add sterile water for injection or bacteriostatic water for injection for reconstitution.

What is claimed is:

1. A compound represented by the formula $$\text{structure showing penem with OH, S, (CH}_2)_n\text{--C(NR'R'')(H)(COOH), and COOH groups}$$

wherein R' and R" are independently hydrogen, lower alkyl, lower alkenyl, phenyl, substituted phenyl wherein the substituents are one or more groups chosen from among chloro, bromo, fluoro, lower alkyl, hydroxy, nitro, amino, aminomethyl, lower monoalkylamino, lower dialkylamino, lower alkoxy and carboxy, heteroaryl of 5 to 7 ring atoms of which 3 to 6 are carbon atoms and the remaining ring atoms are nitrogen, sulfur or oxygen, or R'is hydrogen and R" is $CH_3(CH_2)_pCO-$ or $CH_3(CH_2)_qSO_2-$, wherein p is 0-16 and q is 1-17, or R', R" and the N to which they are attached form a group of the formula

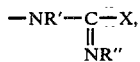

wherein
X is hydrogen, lower alkyl or amino;
n is 0 to 4; and
the pharmaceutically acceptable salts thereof, in racemic or optically active form.

2. A compound represented by formula:

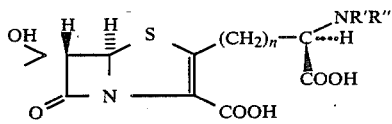

wherein n, R' and R" are as defined in claim 1.

3. A compound of claim 2 wherein R' and R" are each hydrogen.

4. A compound of claim 2 wherein n is 0.

5. A compound of claim 2 wherein n is 1.

6. A compound of claim 2 wherein n is 2.

7. A compound of claim 2 wherein n is 3.

8. A compound of claim 2 wherein n is 4.

9. A compound according to claim 3 wherein n is 2 which is (5R,6S,8R,3'R)-6-(1-hydroxyethyl)-2-(3'-amino-3'-carboxy)propyl-2-penem-3-carboxylic acid.

10. A compound according to claim 3 wherein n is 1 which is (5R,6S,8R,3'R)-6-(1-hydroxyethyl)-2-(2'-amino-2'carboxy)ethyl-2-penem-3-carboxylic acid.

11. A compound according to claim 3 wherein n is 3 which is (5R,6S,8R,4'R)-6-(1-hydroxyethyl)-2-(4'amino-4'-carboxy)butyl-2-penem-3-carboxylic acid.

12. A pharmaceutical composition comprising an effective amount of an antibacterial compound of claim 1 in admixture with a pharmaceutically acceptable carrier.

13. A composition according to claim 12 adapted for oral administration.

14. A composition according to claim 12 adapted for parenteral administration.

15. A composition according to claim 12 adapted for topical administration.

16. A method of treating or preventing bacterial infections in animals which comprises administering a compound of claim 1.

17. A method according to claim 12 wherein the amount administered in 1 to 250 mg/kg of host body weight.

18. A method according to claim 12 wherein the amount administered is from about 5 to 20 mg/kg of host body weight.

* * * * *